(12) United States Patent
Romanov et al.

(10) Patent No.: US 6,979,575 B1
(45) Date of Patent: Dec. 27, 2005

(54) FLUOROCHROMES FOR LABELLING BIOMOLECULES AND POLYMER PARTICLES AND BIOANALYTICAL AND SCREENING METHODS BASED THEREON

(75) Inventors: Nikolai N. Romanov, Kiev (UA); Otto S. Wolfbeis, Regensburg (DE)

(73) Assignee: Chromeon GmbH, Regensburg (DE)

( * ) Notice: Subject to any disclaimer, the term of this patent is extended or adjusted under 35 U.S.C. 154(b) by 280 days.

(21) Appl. No.: 10/304,365

(22) Filed: Nov. 26, 2002

(30) Foreign Application Priority Data

Nov. 26, 2001 (DE) ............................. 101 57 615

(51) Int. Cl.⁷ .................. G01N 33/533; G01N 33/552; C07D 417/06; C07D 209/56; C07K 17/06; C07K 17/04
(52) U.S. Cl. .................... 436/546; 435/6; 435/7.21; 435/7.5; 530/391.5; 530/405; 436/172; 436/503; 436/527; 544/217; 548/440; 548/159
(58) Field of Search ................ 548/440, 159; 436/546, 172, 503, 527; 435/6, 7.1, 7.21, 435/7.5; 530/391.5, 405; 544/217

(56) References Cited

U.S. PATENT DOCUMENTS

| | | | |
|---|---|---|---|
| 3,963,747 A | 6/1976 | Schefczik et al. | |
| 4,201,713 A | 5/1980 | Harnisch | |
| 4,234,488 A | 11/1980 | Harnisch et al. | |
| 4,876,356 A | 10/1989 | Dust et al. | |
| 6,048,982 A | 4/2000 | Waggoner | |

FOREIGN PATENT DOCUMENTS

| | | |
|---|---|---|
| DE | 24 29 760 A | 10/1987 |
| EP | 0 241 696 A2 | 10/1987 |
| JP | 62216792 | 9/1987 |

OTHER PUBLICATIONS

Construction of new nitrogen-containing heterocycles . . . dyes, Briks, et al.—Russian Journal of Organic Chemistry, No. 1, (1994).
Polymethine Dyes Based on Pyrroloanthrone, Briks, et al. Chemistry of Heterocyclic Compounds, No. 10, (1990).

*Primary Examiner*—Mary E. Ceperley
*Assistant Examiner*—Shafiqul Haq
(74) *Attorney, Agent, or Firm*—Fulbright & Jaworski L.L.P.

(57) ABSTRACT

New reactive dyes are described which can be used to fluorescently label bioorganic molecules such as amino acids, proteins, antibodies, nucleotides and also polymer particles. The color of the new dyes and conjugates thereof can be varied over a wide range. In contrast to known symmetric cyanine dyes, the dyes of the invention contain only one reactive group. Hence the labelling takes place without the interfering cross-linking that occurs with bireactive dyes. Their fluorescence quantum yields are very high (especially in the conjugated form). Conjugates thereof with proteins, oligonucleotides or particles can be used in fluorescence-based analytical methods of determination e.g. in immunoassays, in hybridization assays, in cytometry or for pharmaceutical screening.

11 Claims, No Drawings

FLUOROCHROMES FOR LABELLING BIOMOLECULES AND POLYMER PARTICLES AND BIOANALYTICAL AND SCREENING METHODS BASED THEREON

The invention concerns new reactive dyes and their use for the fluorescent labelling of bioorganic molecules or organic particles.

The fluorescent labelling of biomolecules plays an important role in bioanalytics and biological research. A distinction is made between fluorophores which bind non-covalently to biomolecules such as proteins or DNA (e.g. intercalators) and those which can be bound covalently (chemically) to biomolecules.

Numerous fluorescent labels have been described. In general they are fluorescent chromophores which carry a very reactive group which can chemically (covalently) bind to another functional group of a biomolecule. The general reaction scheme for covalent labelling can be described as follows: A reactive group X is located on a fluorophore F and can chemically react with a second reactive group HY located on a biomolecule or particle. Usually a group of the type HX is cleaved off in this process.

F—X+HY-biomolecule ==>F—Y-biomolecule+HX

Alternatively one can provide a dye with a biotin group. Biotin binds with high affinity ($K_d$ ca. $10^{13}$ M) to the proteins avidin and streptavidin (SA). When the SA is located on a biomolecule, it is possible to non-covalently link dyes to biomolecules by means of the biotin-(strept)avidin binding.

In this manner a fluorophore F can be introduced into a biomolecule and it can then in turn be detected by all analytical methods based on fluorescence. Typical examples of the groups X and Y are given in Table 1.

TABLE 1

Reactive groups (X) on synthetic fluorophores which allow them to be coupled to specific groups (Y) on biomolecules or on polymers. In addition the affinity binding between biotin and strept(avidin) listed in the last two rows is also of major importance.

| X (on the fluorophore) | Y (on the biomolecule or particle) | Reaction type (leaving group or new group) |
|---|---|---|
| —SO$_2$Cl | —NH$_2$ | substitution (cleavage of HCl) |
| —CO—CH$_2$—I | —SH | substitution (cleavage of HI) |
| —CO—CH$_2$—Br | —COOH | substitution (cleavage of HBr) |
| —CO—O—SUI[a] | —NH$_2$ (protein) | substitution (cleavage of NHS) |
| —N=C=S | —NH$_2$ (protein) | addition (to form —NH—CS—NH—) |
| —N=C—O | —OH (alcohol) | addition (to form —NH—CO—O—) |
| -phorphoramidite | —OH (deoxyribose) | covalent binding (P—O) |
| -maleinimide | —SH (protein) | covalent addition |
| -(strept)avidin | -biotin | affinity binding |
| -biotin | (strept)avidin | affinity binding |

[a] SUI represents an N-succinimidoyl group

Typical dye groups are for example the reactive dyes described by Waggoner and coworkers in U.S. Pat. Nos. 6,048,982, 5,627,027, 5,569,766, 5,569,587, 5,486,616, 5,268,486 from the group of cyanines having the following general structure:

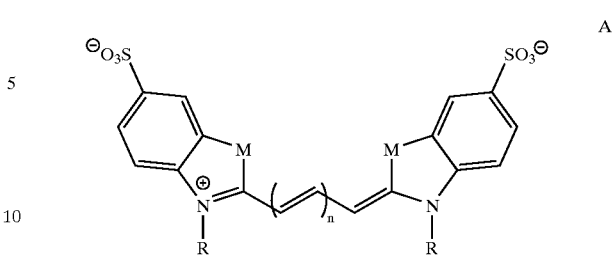

A in which M represents O, S, NR or C(CH$_3$)$_2$. A reactive group (see table 1) is usually located on the residue R which enables binding to a biomolecule.

The colour of such compounds is primarily determined by n (typically 0–3), and also to a lesser extent by the heterocyclic ring or its substituents. In the following 3 compounds (B, C, D) the absorption maximum per n typically increases by 100 mm i.e. from 440 to 560 to 650 nm:

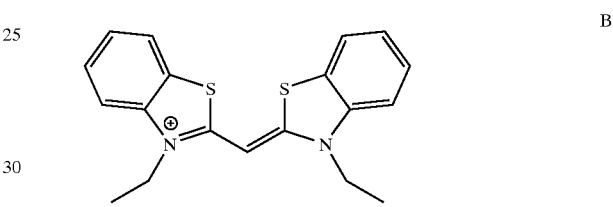

B

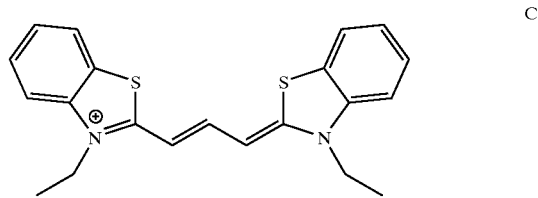

C

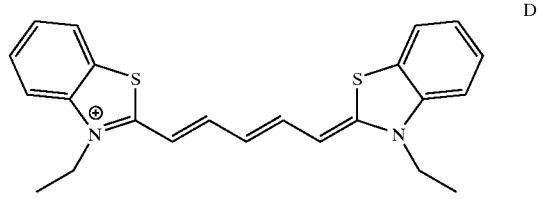

D

However, compounds of this type are relatively photolabile and susceptible to oxidation. This prompted a search for methods to stabilize the compounds by for example incorporating rings which make them more rigid. This yielded for example the following compounds (E, F, G):

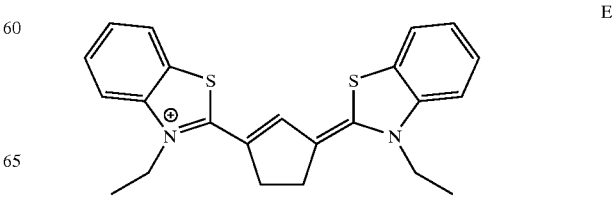

E

-continued

F

G

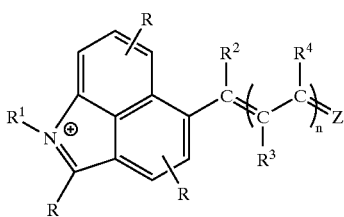

However, these compounds are very laborious to prepare and they become increasingly insoluble in water due to their molecular size which makes them less suitable for applications in bioanalytics. However, a major disadvantage is that such dyes can only be produced in a simply manner when they have a symmetric structure. In the case of reactive markers this means that two reactive groups are always also present. This is unnecessary and often even undesirable since the two groups can result in a very disadvantageous cross-linking of biomolecules by such bireactive dyes.

Hence an object of the present invention was to provide new marker dyes which have a high photostability and at the same time are simple to prepare. Furthermore it should be possible to provide the new marker dyes with only one reactive group.

It was now found that unsymmetric and monoreactive dyes having a considerably improved photostability can be obtained in a relatively simple manner when the chromophore is positioned in a novel manner by means of an aromatic (or heteroaromatic) ring. An advantage of the new dyes is that they are very photostable, and preferably only have one reactive group (corresponding to X in table 1) and that the monoreactive dyes are relatively easy to prepare. They have the general chemical structure 1,

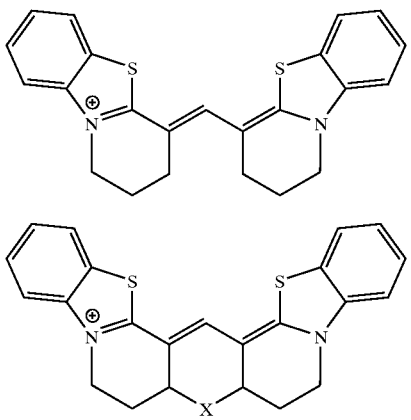

1 in which
R each independently of one another represents H or any organic substituent or ring which in particular does not quench the fluorescence of the system,
$R^1$ to $R^4$ each independently of one another can represent H, an optionally substituted, linear, branched or cyclic, saturated or monounsaturated or polyunsaturated alkyl residue or an optionally substituted aryl residue,
$R^2$ to $R^4$ can also represent a halogen, cyano or optionally substituted amino group, R and $R^1$ to $R^4$ can also optionally be linked together by means of heterocyclic rings;
Z represents any divalent aromatic or heteroaromatic residue which can also contain a residue R as defined above,
n can have values between 0 and 3 and
at least one residue R or $R^1$ to $R^4$ contains any group (including a biotin group) which enables a biomolecule or a particle to be labelled.

R preferably represents a substituent having 1 to 30 C atoms, preferably 1 to 12 C atoms or a ring (system) having 5 to 30 and in particular 6 to 12 C atoms. Particularly suitable residues are for example $C_1$–$C_{12}$ alkyl residues and aryl residues especially a phenyl residue. The residues R are preferably selected such that they do not quench the fluorescence of the system.

$R^1$ to $R^4$ preferably represent a $C_1$ to $C_{12}$ residue and most preferably H. The substituents on the alkyl residue and aryl residue are preferably selected from hydroxy, halogen, $C_1$–$C_6$ alkoxy and amino.

$R^2$ to $R^4$ can additionally also represent halogen, cyano or an optionally substituted amino group in which case the substituents are preferably selected from $C_1$–$C_8$ hydrocarbon groups in particular alkyl groups and $C_1$–$C_8$ hydroxyalkyl groups.

Two or more of the residues R, $R^1$, $R^2$, $R^3$ and $R^4$ can also be linked together to form ring systems and especially heterocyclic rings which contain at least one atom selected from N, O, S or P.

Z in formula 1 represents a divalent aromatic or heteroaromatic residue which can preferably have 5 to 30 C atoms and in particular 5 to 12 C atoms. The heteroatoms are advantageously selected from N, O, S and P. The residue Z can in turn be monosubstituted or polysubstituted with residues R as defined above.

The dyes according to the invention are additionally characterized in that at least one residue R, $R^1$, $R^2$, $R^3$ or $R^4$ contains a group which enables the labelling of a biomolecule on a particle. Such a group is in particular suitable for binding covalently to a reactive group on a biomolecule or a particle or is able to interact with a biomolecule or a particle. Suitable reactive groups which enable a labelling are for example —$SO_2Cl$, a reactive ester of a carboxylic acid, a haloacetyl of formula CO—$CH_2$—X where X represents halogen, such as —CO—$CH_2$—I, —CO—$CH_2$—Br, a chlorotriazine, —CO—O—N-succinimidoyl, —N=C=S, N=C=O, a pyrilium group, phosphoramidite, maleinimide, (strept)avidin or biotin.

Suitable biomolecules which can be labelled include proteins, antibodies, DNA, RNA, PNA, pharmaceutical agents, sugars, cells, tissue sections or organic particles having a diameter between 0.01 μm and 10 μm.

The fluorescent marker dyes according to the invention are additionally characterized in that the molecule may contain an ionic group, preferably a sulfo, sulfate, phosphate, phosphonate or quarternary ammonium group.

Surprisingly the new chromophore also has another positive effect i.e. a shift of the absorption maximum into the red wavelength range. This is shown by comparing the absorption maxima of the following two dyes H and I:

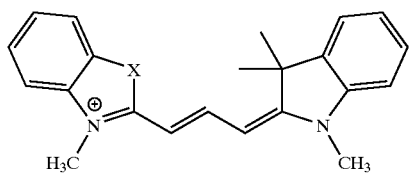

H

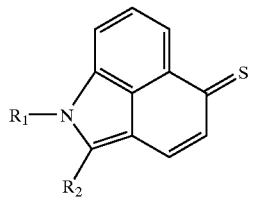

III

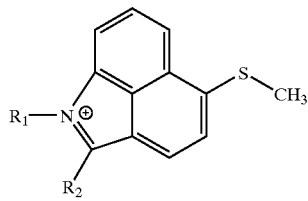

IV

The first (H; X=S) has an absorption maximum at 542 nm (in ethanol), the second at 545 nm, although the new molecule I according to the invention has a shorter system (only 3 C atoms) between the chromophoric end groups (i.e. the two nitrogen atoms).

This applies in a similar manner to the following two dyes J and K,

The compounds IV can for example be reacted with quaternized benzthiazoles of structure V (in which X=H or sulfo) to yield the dyes of the type VI:

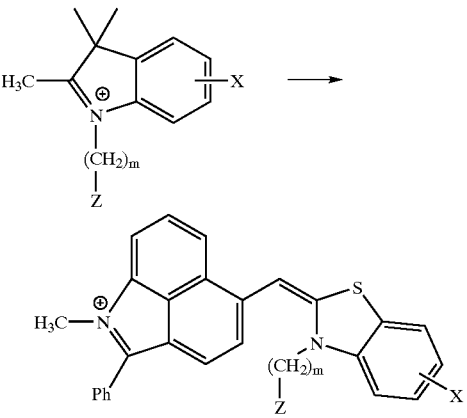

Z = COOH       m = 5
Z = CO—O—SUI  m = 5
Z = OH         m = 6
Z = PAM        m = 6 whose absorption maxima are at 650 and 658 nm respectively i.e. they are not very different despite the different lengths of the molecules.

The new dyes are preferably synthesized according to the methods described in the following: The cationic thioethers of type IV are formed from the 5 (1H)benzo(c,d)indol-5-ones of type II via the thio compounds of type III:

In order to conjugate the above-mentioned dye class it is necessary to convert them into a reactive form. This is accomplished by introducing one of the reactive groups listed in table 1. Thus for example a sulfo group (compound VI; $X=SO_3^-$) can be converted into its sulfochloride.

If for example n=5 and Z=COOH in compound VI then this is a coloured or fluorescent dye which can easily be converted into a reactive N-hydroxysuccinimide ester:

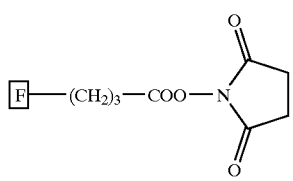

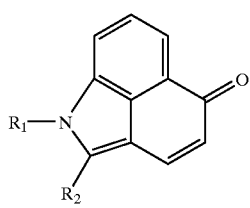

II

This NHS ester reacts for example with amino groups of biomolecules as follows:

In this manner biomolecules labelled with F are obtained.

If in contrast an OH group is selected as Z in compound VI, it can be activated via a phosphoramidite group in such a manner that it forms stable conjugates with riboses or deoxyriboses. For this purpose the alcohol fluorophore F—$(CH_2)_n$—OH is firstly reacted with a phosphoramidite (I) to form II which is then reacted with a protected nucleoside in a known manner to form III. After oxidation with iodine, one obtains fluorescent-labelled nucleosides of type IV. This reaction is shown in the following where B represents a nucleobase.

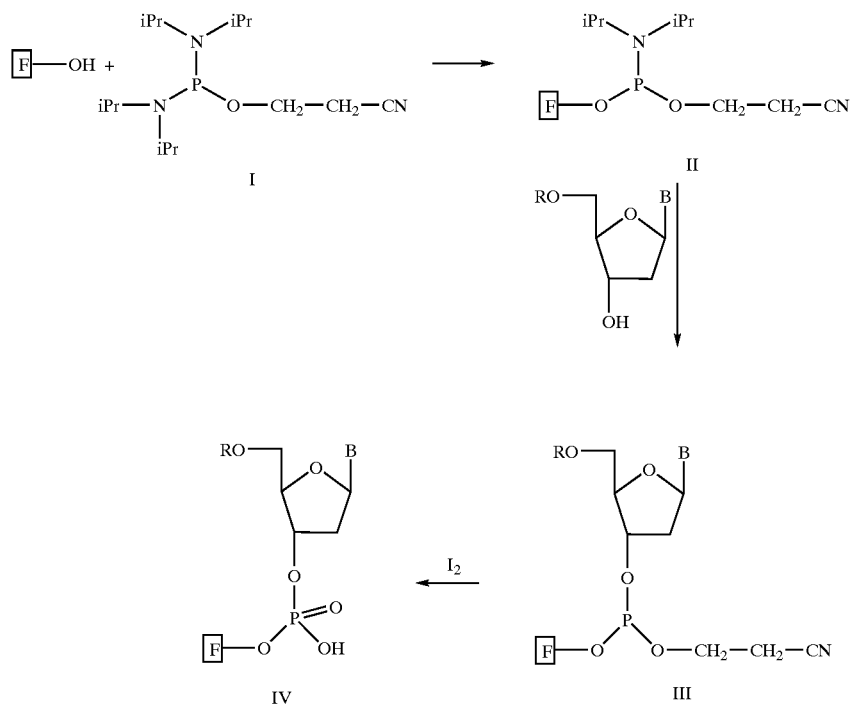

EXAMPLES

The following are examples of the preparation of chromophores according to the invention, their application for labelling biomolecules and their applications in methods for determining biomolecules based on fluorescence analysis. The methods of determination can be carried out using. e.g. a microtitre plate, a flow cytometer or another automated or automatable laboratory method.

Example 1

Preparation of 1-methyl-2-phenyl-5 (1H)-benzo[c,d]indolone (Compound 259)

2.51 g dimethyl sulfate is added dropwise to a solution of 2.45 g (10 mmol) 5-hydroxy-2-phenylbenzo[c,d]indole in 50 ml 10% sodium hydroxide solution. It is stirred for 2 hours which results in the formation of a precipitate which is filtered. Yield 2.18 g (61%) pale yellow crystals having a melting point of >250° C.

Example 2

Preparation of 1-methyl-2-phenyl-5 (1H)-benzo[c,d]indole-thione (Compound 275)

A mixture of 2.6 g (10 mmol) 1-methyl-2-phenyl-5 (1H)-benzo[c,d]indolone (see above), 10 ml pyridine and 2.3 g $P_2S_5$ is vigorously stirred for 1 hour at 100° C. Then it is poured into 100 ml water and the precipitate is removed by filtration. Yield: 2.1 g (76%) yellowish crystals having a melting point of >250° C.

Example 3

Preparation of 1-methyl-5-methylthio-2-phenyl-benzo[c,d]indolium-iodide (Compound 417)

A mixture of 2.75 g (10 mmol) 1-methyl-2-phenyl-5 (1H)-benzo[c,d]indole-thione (compound 275), 10 ml dry acetone and 2.85 (20 mmol) methyl iodide is refluxed for 2 hours. Then it is cooled and the resulting precipitate is filtered (1.75 g; 42%). Yellow crystals, melting point>250° C.

Example 4

Preparation of 1-[5-(3-methyl-2(3H)benzothiazolylidene)-methyl-2-phenyl-benzo[ c,d]indolium] Butyric Acid Iodide (Compound 532)

A mixture of 420 mg (1 mmol) of 1-methyl-5-methylthio-2-phenyl-benzo[c,d]indolium iodide, 10 ml dry ethanol, 290 mg (1 mmol) 4-(2-methyl-1-benzthiazolium) butyric acid iodide and 100 mg (1 mmol) triethylamine is boiled for 10 min. It is then cooled and the red precipitate is filtered. Yield: 410 mg (70%) red crystals; melting point>250° C.

Example 5

Preparation of a Reactive NHS Ester (Compound 532-NHS)

14 mg dicyclohexyl carbodiimide (DCC) and 8 mg N-hydroxysuccinimide (NHS) were dissolved in 1 ml dry and freshly distilled dimethylformamide (DMF). 20 mg of compound 532 (see above) also dissolved in 1 ml DMF was added. The solution was stirred for 8 hours at room temperature and then filtered. The solvent was removed under a vacuum and the residue was purified on an RP chromatographic column (mobile solvent methanol). The red-violet solution was concentrated by evaporation and the residue was dried over $P_2O_5$. Yield 20 mg (86%) of a red-violet crystal mass.

Example 6

Preparation of a Biotin Conjugate (Compound 532-Biotin)

14 mg dicyclohexyl carbodiimide (DCC) and 8 mg N-hydroxysuccinimide (NHS) were dissolved in 1 ml dry and freshly distilled dimethylformamide (DMF). 20 mg of compound 532 (see above) also dissolved in 1 ml DMF was added to this. This solution was then slowly passed into an aqueous solution which consisted of a solution of 8.4 mg biotin hydrazide (Sigma, prod. No. B-7639) or biotin-ethylenediamine (=N-(2-aminoethyl)biotinamide hydrobromide; product No. A-1593 from Molecular Probes; Portland, Oreg.) in 10 ml phosphate buffer pH 8.0. It was allowed to stand for 2 h at 25° C., a few drops of 1 M hydrochloric acid are added and the solvent is almost completely removed. The solid product is dissolved in methanol and purified by gel chromatography on a 20 cm Sephadex column (G50).

Example 7

Labelling of Human Serum Albumin with the Reactive Dye 532-NHS 1 mg of the NHS ester 532-NHS was dissolved in 100 µl anhydrous DMF. At the same time 5 mg human serum albumin (HSA) was dissolved in 1 ml of a 50 mmol/l bicarbonate buffer solution pH 9.0. The DMF stock solution was now added to the protein solution in small portions (30 µl) while stirring. After the addition was completed it was stirred for a further 5 h.

Unconjugated dye was separated from the labelled protein by gel permeation chromatography with 22 mmol/l phosphate buffer pH 7.2. The red band which ran fastest contained the labelled protein.

Example 8

Labelling of an Amino-Modified Nucleic Acid Oligomer

The amino-modified 15-oligomer 3'-TAA-TGG-CCT-GAG-ATAT-$(CH_2)_6$—$NH_2$ was reacted with the reactive dye 532-NHS in the following manner: The oligomer (0.2 mg) was dissolved in 5 ml acetonitrile and heated to 50° C. Afterwards a solution of 0.1 mg of the dye in 1 ml acetonitrile was slowly added dropwise. After 1 h the acetonitrile was removed by evaporation and the residue was subjected to a polyacrylamide electrophoresis. The oligomer and remaining (excess) dye can easily be separated.

Example 9

Labelling of Glass Microparticles

Porous glass beads (1.0 g; pore size 70 nm; with aminopropyl groups on the surface (40–100 µmol per gram beads; obtained from Sigma, product No. G-5019) were suspended in bicarbonate buffer solution pH 8.0. A solution of 3 mg of the dye 532-NHS in DMF was slowly added dropwise at 50° C. while stirring rapidly. After one hour the red stained glass particles were separated and washed with copious amounts of distilled water, 1% acetic acid and again washed with water until the dye was no longer detected in the wash water. Afterwards the particles were dried and stored in a dry state. The red coloured particles had a strong yellow-green fluorescence.

Example 10

Labelling of a Protein with a Biotin Dye

The labelling was carried out by means of the biotin-streptavidin binding reaction. Polyclonal anti-HSA (goat; Sigma product No. A-1151) was diluted 10-fold in phosphate buffer and firstly labelled with streptavidin maleinimide (Sigma, product No. S-9415) according to the instructions of Duncan et al., in Analytical Biochemistry 132 (1983) 68. To the streptavidin/anti-HSA conjugate formed in this manner was added the biotin-reagent 532-biotin (see above) after electrophoretic purification in buffer solution (pH 7.0) and electrophoretically purified after standing for 2 h at room temperature. In this manner an orange-red antibody is obtained with a weak yellow-green fluorescence.

What is claimed is:

1. A colored and fluorescent marker dye having an absorption maximum between 420 and 950 nm of formula:

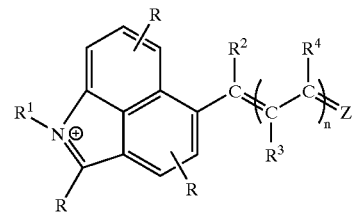

in which
R represents H or an organic substituent or ring
$R^1$ or $R^4$ can represent H, an optionally substituted linear, branched or cyclic, saturated or unsaturated alkyl residue or an optionally substituted aryl residue,
$R^2$ to $R^4$ can also represent a halogen, cyano or optionally substituted amino group,
R and $R^1$ to $R^4$ can also optionally be linked together by means of carbocyclic or heterocyclic rings;
Z represents a divalent aromatic or heteroaromatic residue which can also contain a residue R as defined above, n can have a value between 0 and 3 and at least one residue R or $R^1$ to $R^4$ contains a group which enables a biomolecule or a particle to be labeled.

2. The fluorescent marker dye of claim 1, characterized in that at least one of the substituents R or $R^1$ to $R^4$ can covalently or non-covalently bind the marker dye to a biomolecule.

3. The fluorescent marker dye of claim 1, characterized in that at least one substituent R is either a reactive ester of a carboxylic acid, a maleinimide, a haloacetyl of the type —CO—CH$_2$—X where X represents halogen, a sulfochloride, a chlorotriazine, an —SCN or —OCN group, a pyrylium group or a biotin is present on at least one of the substituents R or $R^1$ to $R^4$.

4. The fluorescent marker dye of claim 1, characterized in that the molecule contains an ionic group.

5. The fluorescent marker dye of claim 4, wherein said ionic group is a sulfo, sulfate, phosphate, phosphonate or quarternary ammonium group.

6. Method for making a fluorescently labeled biomolecule comprising attaching the fluorescent marker dye of claim 1 to said biomolecule.

7. The method of claim 6, wherein said biomolecule is a protein, an antibody, DNA, RNA, PNA, a pharmaceutical agent, a sugar, a cell, a tissue section, or an organic particle having a diameter between 0.01 μm and 10 μm.

8. A fluorescent biomolecule labeled with the fluorescent marker dye of claim 1.

9. A method for determining presence of a substance in a sample, comprising contacting a sample with a biomolecule of claim 8 and determining binding of said biomolecule to said substance fluorescently as a determination of said substance in a sample.

10. The method of claim 9, comprising determining binding via measuring intensity, decay time, efficiency of energy transfer or fluorescence polarity.

11. The method of claim 9 comprising determining said substance in a sample with a microlitre plate, a flow cytometer, or via an automated or automatable method.

* * * * *